US011195599B2

(12) United States Patent
Bastide et al.

(10) Patent No.: US 11,195,599 B2
(45) Date of Patent: Dec. 7, 2021

(54) DETERMINING SOURCES OF HEALTHCARE EXPERTISE RELATED TO A CONDITION OF THE PATIENT

(71) Applicant: International Business Machines Corporation, Armonk, NY (US)

(72) Inventors: Paul R. Bastide, Boxford, MA (US); Matthew E. Broomhall, Goffstown, NH (US); Robert E. Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 678 days.

(21) Appl. No.: 15/247,362

(22) Filed: Aug. 25, 2016

(65) Prior Publication Data

US 2018/0060493 A1 Mar. 1, 2018

(51) Int. Cl.
*G16H 10/60* (2018.01)
*G16H 80/00* (2018.01)
*G16H 50/70* (2018.01)
*G16H 40/20* (2018.01)
*G06Q 10/10* (2012.01)

(52) U.S. Cl.
CPC ............ *G16H 10/60* (2018.01); *G16H 40/20* (2018.01); *G16H 50/70* (2018.01); *G16H 80/00* (2018.01); *G06Q 10/1095* (2013.01)

(58) Field of Classification Search
CPC .... G06F 19/00; G06F 19/3418; G06F 19/328; G06F 19/3456; G06F 19/321;
(Continued)

(56) References Cited

U.S. PATENT DOCUMENTS 7,792,786 B2   9/2010  Chen et al.
9,171,083 B2  10/2015  Blumenfeld et al.
(Continued)

OTHER PUBLICATIONS

"Grand Rounds Launches "Office Visits" Service, Enabling People to Find Precisely the Right Doctor Within Local Travel Distance . . . " Marketwire , Apr. 8, 2014 (Year: 2014).*
(Continued)

*Primary Examiner* — Rachel L. Porter
(74) *Attorney, Agent, or Firm* — Will Stock; Edell, Shapiro & Finnan, LLC (57) ABSTRACT

A method, a system, and a computer program product are provided. Electronic health records of patients, indicating encounters with healthcare providers for medical conditions, are analyzed to determine networks of healthcare providers. Based on the analyzing, healthcare provider network data corresponding to a graphical representation of the determined networks of healthcare providers are generated. The healthcare provider network data includes multiple paths, each of which indicates a series of healthcare providers. Based on the generated healthcare provider network data, a path indicating a series of healthcare providers within the healthcare provider network data and corresponding to at least one medical condition indicated by an electronic health record of a patient is identified. An action for the patient and a corresponding healthcare provider to perform the action is determined based on the identified path. An appointment is automatically scheduled for the patient with the corresponding healthcare provider.

20 Claims, 7 Drawing Sheets

(58) Field of Classification Search
CPC ............ G06F 19/3481; G06F 19/3475; G06F 17/30247; G06F 17/30268; G06F 17/3028; G06F 19/325; G06F 19/326; G06F 3/0482; G06F 3/04842; G06F 11/3664; G06F 17/30241; G06F 17/30342; G06F 17/30477; G06F 17/30528; G06F 17/3053; G06F 17/30554; G06F 17/30569; G06F 17/30876; G06F 17/3097; G06F 17/40; G16H 10/60; G16H 40/20; G16H 50/20; G16H 80/00; G16H 10/20; G16H 15/00; G16H 40/63; G16H 50/30; G16H 10/65; G16H 50/70; G16H 20/30; G16H 20/60; G16H 50/50; G16H 10/00; G16H 10/40; G16H 20/10; G16H 20/40; G16H 20/70; G16H 40/67; G16H 50/00; G06Q 10/10; G06Q 10/00; G06Q 10/107; G06Q 30/00; G06Q 50/01; G06Q 10/06; G06Q 50/22; G06Q 10/06375; G06Q 10/06393; G06Q 10/109; G06Q 10/1093; G06Q 20/10; G06Q 20/102; G06Q 40/02; G06Q 40/08; G06Q 10/047; G06Q 10/06316; G06Q 10/101

See application file for complete search history.

(56) References Cited

U.S. PATENT DOCUMENTS

| | | | |
|---|---|---|---|
| 2001/0051881 A1 | 12/2001 | Filler | |
| 2006/0074980 A1* | 4/2006 | Sarkar | G06F 16/958 |
| 2006/0080140 A1 | 4/2006 | Buttner et al. | |
| 2008/0183497 A1* | 7/2008 | Soon-Shiong | G16H 70/00 705/2 |
| 2010/0106518 A1* | 4/2010 | Kuo | G16H 40/20 705/2 |
| 2010/0153832 A1* | 6/2010 | Markus | G06F 16/245 715/205 |
| 2011/0040576 A1* | 2/2011 | Madan | G16H 70/20 705/3 |
| 2013/0073313 A1* | 3/2013 | Christakis | G06Q 30/00 705/2 |
| 2014/0108030 A1* | 4/2014 | Tejeda-Monteagut | G06Q 10/1095 705/2 |
| 2014/0257852 A1* | 9/2014 | Walker | G06F 19/3456 705/3 |
| 2014/0358574 A1* | 12/2014 | Tara | G16H 40/20 705/2 |
| 2015/0242583 A1* | 8/2015 | Edson | G16H 50/20 705/3 |
| 2015/0317436 A1 | 11/2015 | Kutty | |
| 2015/0356247 A1* | 12/2015 | Kolowitz | G06F 19/00 705/3 |
| 2017/0011194 A1* | 1/2017 | Arshad | G16H 10/60 |
| 2017/0061086 A1* | 3/2017 | Pecora | G06Q 10/0635 |
| 2017/0169173 A1* | 6/2017 | Snow, Jr. | G06F 19/324 |

OTHER PUBLICATIONS

Carstens J; Ttl: Platform for offering, selecting and assigning healthcare services to patients; Oct. 10, 2006 Database: ip.com; ip.com No. IPCOM000140614D.

* cited by examiner

DETERMINING SOURCES OF HEALTHCARE EXPERTISE RELATED TO A CONDITION OF THE PATIENT

BACKGROUND

Present invention embodiments are related to systems, methods and computer program products for determining sources of healthcare expertise regarding at least one medical condition of a patient.

An electronic health record (EHR) is an electronic version of a patient's medical history that is maintained by a healthcare provider over time, and may include all key administrative clinical data relevant to care of the patient under a particular healthcare provider, including demographics, progress notes, problems, medications, vital signs, past medical history, immunizations, laboratory data and radiology reports. The EHR allows access to medical information to be automated and can help a clinician streamline workflow. The EHR can support other care-related activities directly or indirectly through various interfaces including evidence-based decision support, quality management and outcomes reporting.

Often, when a patient seeks healthcare, a healthcare provider engages with the patient for a limited time. As a result, the healthcare provider may recommend immediate, and sometimes inaccurate, decisions regarding next steps for the patient to take.

Current expertise location systems use a skills matrix or natural language content to drive a scoring system. However, such scoring systems are susceptible to disclosure of private information and are not ideal for a patient health system.

SUMMARY

In a first aspect of various embodiments, a computer-implemented method is provided. Patients' electronic health records, indicating encounters with healthcare providers for medical conditions, are analyzed to determine networks of healthcare providers. Healthcare provider network data, corresponding to a graphical representation of the determined networks of healthcare providers, are generated. The healthcare provider network data includes multiple paths, each of which indicates a series of healthcare providers. A path indicating a series of healthcare providers within the healthcare provider network data is identified based on the generated healthcare provider network data. The path corresponds to at least one medical condition indicated by an electronic health record of a patient. An action for the patient and a corresponding healthcare provider to perform the action is determined based on the identified path. An appointment is automatically scheduled for the patient with the corresponding healthcare provider.

In a second aspect of the various embodiments, a system for processing electronic health records is provided. The system includes at least one processor and at least one memory connected to the at least one processor. The at least one memory includes instructions stored therein for the at least one processor to configure the system to: analyze electronic medical records of patients indicating encounters with healthcare providers for medical conditions in order to determine networks of healthcare providers; generating healthcare provider network data corresponding to a graphical representation of the determined networks of healthcare providers, wherein the healthcare provider network data includes multiple paths, each of which indicates a series of healthcare providers; identifying a path indicating a series of healthcare providers within the healthcare provider network data corresponding to at least one medical condition indicated by an electronic health record of a patient; determining an action for the patient and a corresponding healthcare provider to perform the action based on the identified path; and automatically scheduling an appointment for the patient with the corresponding healthcare provider.

In a third aspect of various embodiments, a computer program product is provided. The computer program product includes at least one computer readable storage medium that has computer readable program code embodied therewith for execution on a processing system. The computer readable program code is configured to be executed by the processing system to: analyze electronic health records of patients indicating encounters with healthcare providers for medical conditions in order to determine networks of healthcare providers; generating healthcare provider network data corresponding to a graphical representation of the determined networks of healthcare providers, wherein the healthcare provider network data includes multiple paths, each of which indicates a series of healthcare providers; identifying a path indicating a series of healthcare providers within the healthcare provider network data corresponding to at least one medical condition indicated by an electronic health record of a patient; determining an action for the patient and a corresponding healthcare provider to perform the action based on the identified path; and automatically scheduling an appointment for the patient with the corresponding healthcare provider.

BRIEF DESCRIPTION OF THE DRAWINGS

Generally, like reference numerals in the various figures are utilized to designate like components.

DETAILED DESCRIPTION

Figure 1:
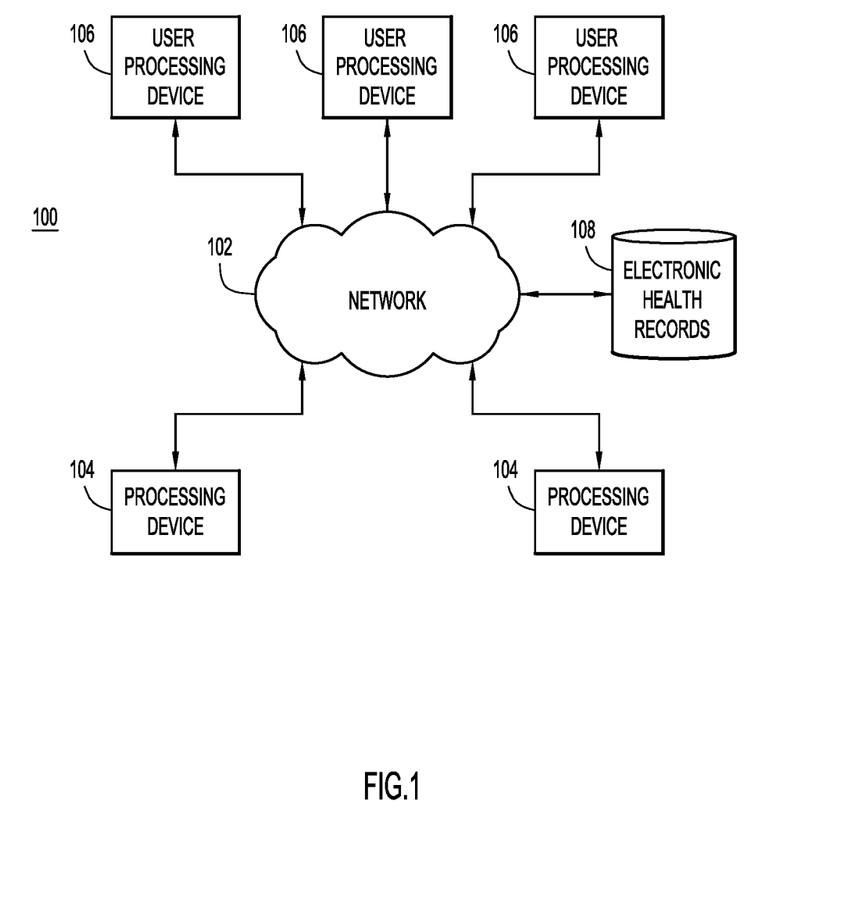
FIG. 1 illustrates an example environment in which embodiments of the invention may be implemented.

With reference now to FIG. 1, an example environment 100 for implementation of embodiments is shown. Environment 100 may include a network 102, one or more processing devices 104, one or more user processing devices 106, and electronic health records 108 on a file server (not shown). Network 102 may be implemented by any number of any suitable communications media (e.g., wide area network (WAN), local area network (LAN), Internet, Intranet, etc.). One or more processing devices 104 and one or more user processing devices 106 may be connected to network 102. One or more processing devices 104 may have access to electronic health records 108 via network 102. In some implementations, electronic health records 108 may be local to one or more processing devices 104. One or more user devices 106 may communicate with one or more processing devices 104 via a network 102. User processing device 106 may be a processing device or processing system of a healthcare provider.

Figure 2:
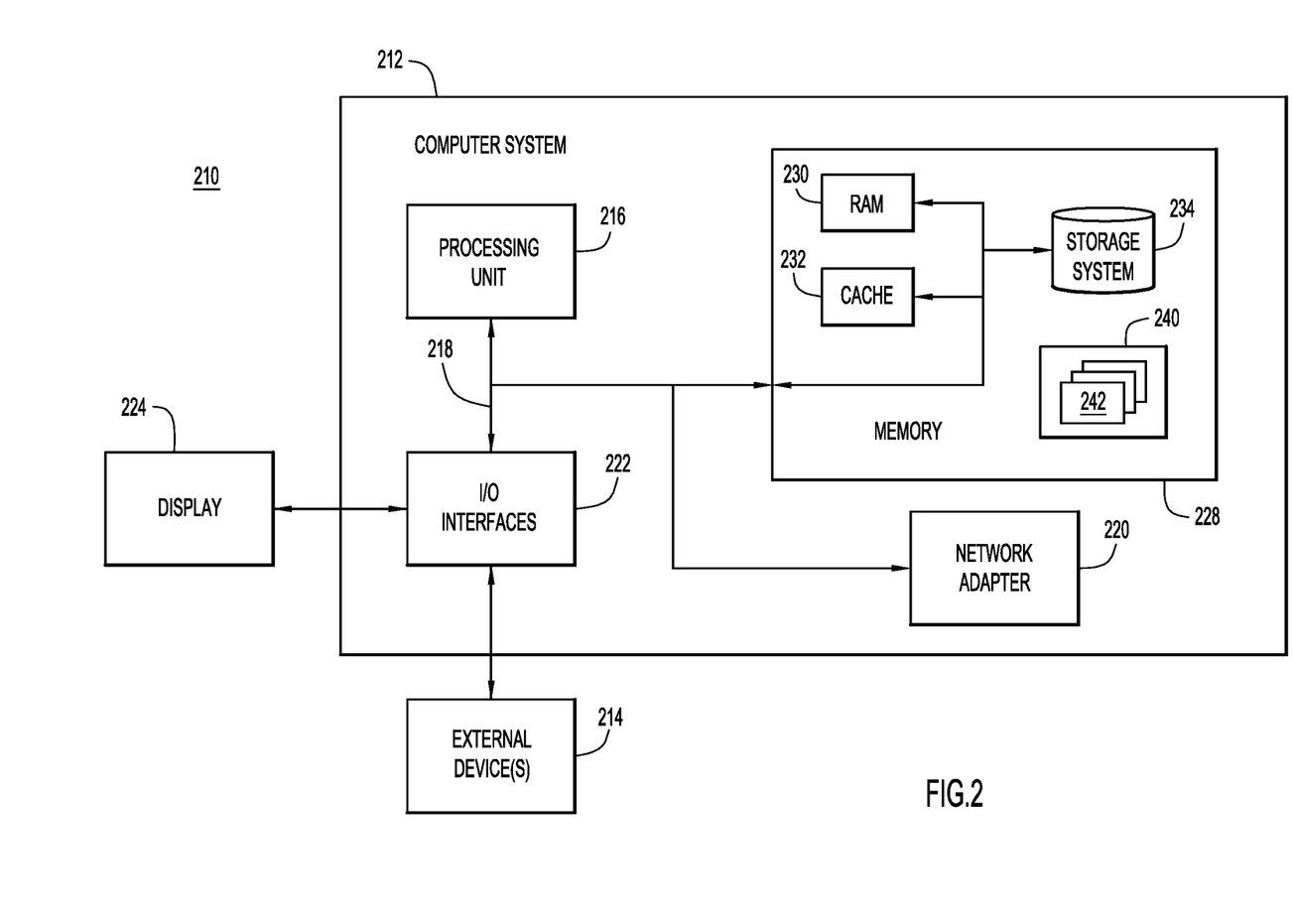
FIG. 2 illustrates an example processing device, or computer system, which may implement various embodiments of the invention.

Referring now to FIG. 2, a schematic of an example processing device 210, which may implement a processing device of one or more processing devices 104 and/or a processing device of one or more user processing device 106, is shown. Processing device 210 is only one example of a suitable processing device for the environment of FIG. 1 and is not intended to suggest any limitation as to the scope of use or functionality of embodiments of the invention described herein. Regardless, processing device 210 is capable of being implemented and/or performing any of the functionality set forth herein.

In processing device 210, there is a computer system 212 which is operational with numerous other general purpose or special purpose computing system environments or configurations. Examples of well-known computing systems, environments, and/or configurations that may be suitable for use with computer system 212 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules, being executed by a computer system. Generally, program modules may include routines, programs, objects, components, logic, data structures, and so on that perform particular tasks or implement particular abstract data types. Computer system 212 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system 212 is shown in the form of a general-purpose computing device. Components of computer system 212 may include, but are not limited to, one or more processors or processing units 216, a system memory 228, and a bus 218 that couples various system components including system memory 228 to one or more processors 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and includes both volatile and non-volatile media, removable and non-removable media.

System memory 228 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, when implementing processing device 104, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and program data or some combination thereof, may include an implementation of a networking environment. When implementing processing device 104, program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 220. As depicted, network adapter 220 communicates with the other components of computer system 212 via bus 218. It should be understood that, although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
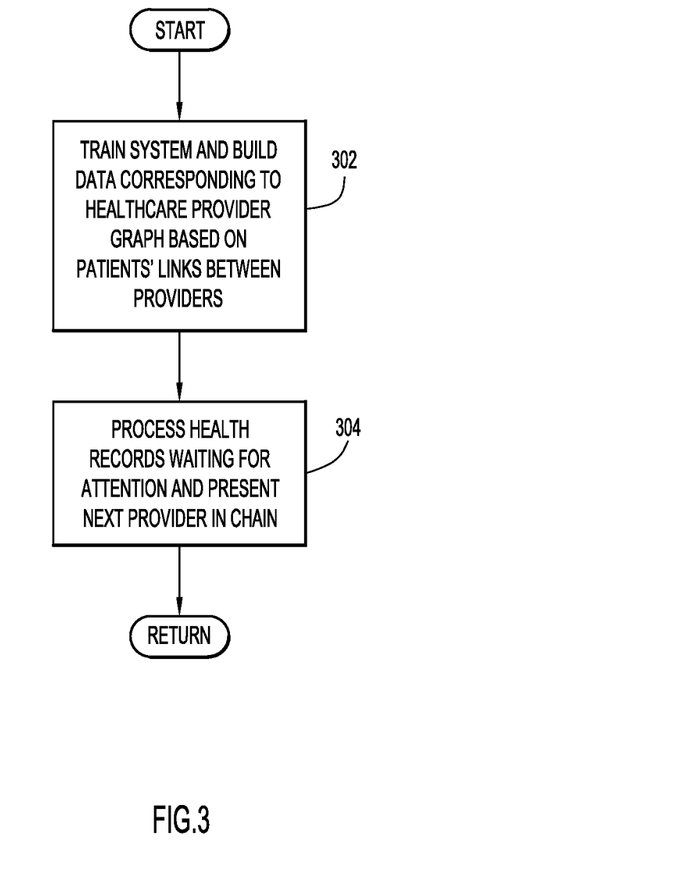
FIG. 3 shows a flowchart of an example process for building data corresponding to a healthcare provider graph and for processing health records waiting for attention.

FIG. 3 is a high-level flowchart of an example process for building data corresponding to a healthcare provider graph and for processing health records waiting for attention, which may be performed in various embodiments of processing device 104. The process may begin by training a processing system and building data corresponding to a healthcare provider graph based on patients' links between healthcare providers, as indicated in electronic health records (act 302). Electronic health records waiting for attention may then be processed and a next provider in a chain of healthcare providers may be determined and presented for each processed healthcare record (act 304).

Figure 4:
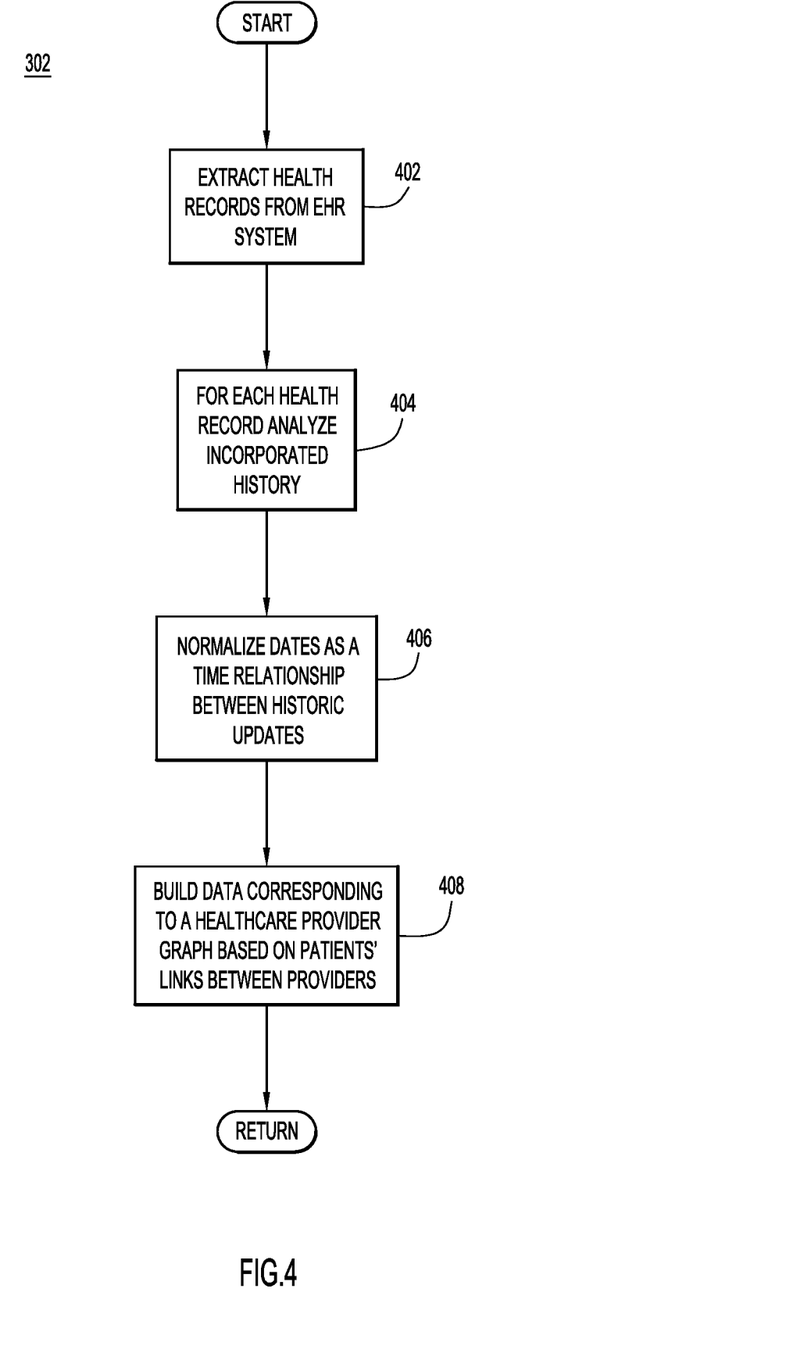
FIG. 4 is a flowchart illustrating example processing of act 302 of FIG. 3.

FIG. 4 is a flowchart illustrating processing that may occur during act 302. The process may begin by extracting health records from an electronic health record (EHR) system (act 402). For each extracted health record, analyze an incorporated history indicating encounters with healthcare providers for one or more medical conditions in order to determine networks of healthcare providers (act 404). In some embodiments, analysis may be limited to data from a specific time period such as, for example, a last one year period of data, a last 5 year period of data, a time period equal to a lifetime of all electronic health records, or some other time period. In addition, the determined networks of healthcare providers may further include networks of healthcare providers who fulfill a same function.

Dates of the encounters with the healthcare providers may then be normalized as a time relationship between historic updates (act 406). For example, a first appointment on January 1 of a given year may be normalized to day 0. Next, data corresponding to a healthcare provider graph based on various medical conditions and patients' links between providers may be built (act 408). Graph edges may have multiple attributes associated therewith, including, but not limited to, role, provider, cause, reason, and action. When creating the graph edges, various embodiments may take into account providers' schedules and availability. In some embodiments, the providers' availability may be weighted. In other embodiments, if one provider is not available, another provider who fulfills a same role and is available may be substituted. Some of the other embodiments may substitute one provider for another only if the one provider's record of successful outcomes is no more than a given percentage less than the another provider's record of successful outcomes. Thus, in such embodiments, if the another provider has a 95% record of successful outcomes and the given percentage is 5%, then the one provider, who may be substituted for the another provider, must have a record of successful outcomes that is greater than or equal to 90%. Of course, the given percentage may have other values such as, for example, 2%, 1%, 0% or another value.

Figure 5:
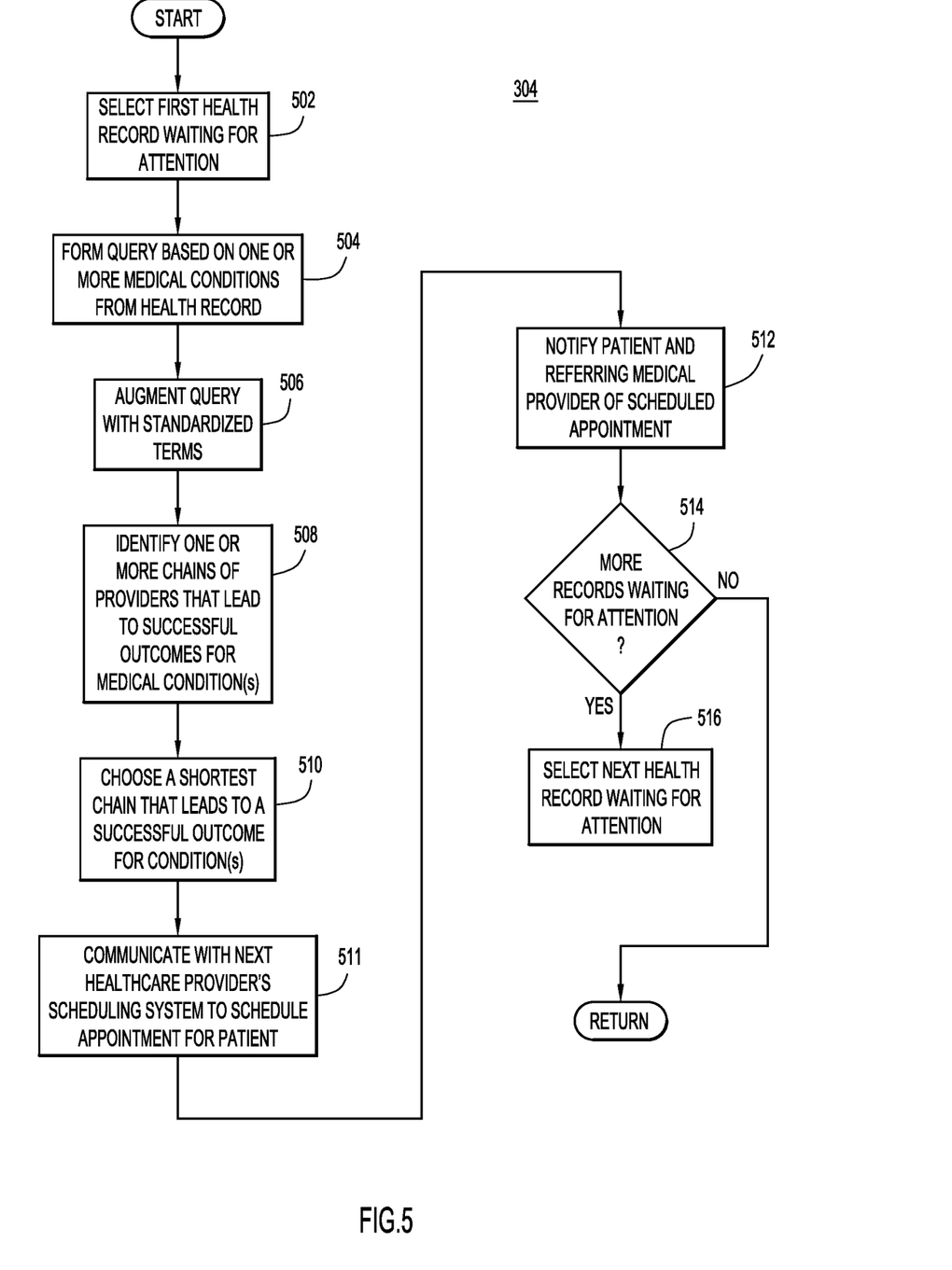
FIG. 5 is a flowchart illustrating example processing of act 304 of FIG. 3.

FIG. 5 is a flowchart that illustrates in more detail a process of act 304. A first electronic health record (EHR) waiting for attention may be selected (act 502). A query may be performed based on one or more medical conditions from the electronic health record (act 504). Next, the query may be augmented with natural language and/or search terms (act 506). In some embodiments, the augmentation may effectively include standard terms for the one or more medical conditions from the healthcare record. For example, a medical condition such as "heart attack" may be augmented with a term, "myocardial infarction." Thus, the augmentation may function to standardize names of medical conditions.

Next, one or more chains of healthcare providers that lead to successful outcomes for the one or more medical conditions from the healthcare record may be identified (act 508). A shortest chain in the healthcare provider graph that leads to a successful outcome for the one or more medical conditions may then be chosen (act 510) and a next provider in a chain of providers may be determined. The shortest chain in the healthcare provider network may be an optimal path leading to the successful outcome for the one or more medical conditions. The system may then communicate with a scheduling system of the next provider in the chain of providers to automatically schedule an appointment with the next healthcare provider for the patient (act 511). The system may then notify the patient and the referring provider regarding the scheduled appointment (act 512). The notification may be through an email message, a text message, a voicemail message, a phone call, or via another method.

A determination may then be made regarding whether more electronic health records are waiting for attention (act 514). If no additional health records are waiting for attention, then the process is completed. Otherwise, a next healthcare record waiting for attention may be selected (act 516) and acts 504-514 may be repeated.

Figure 6:
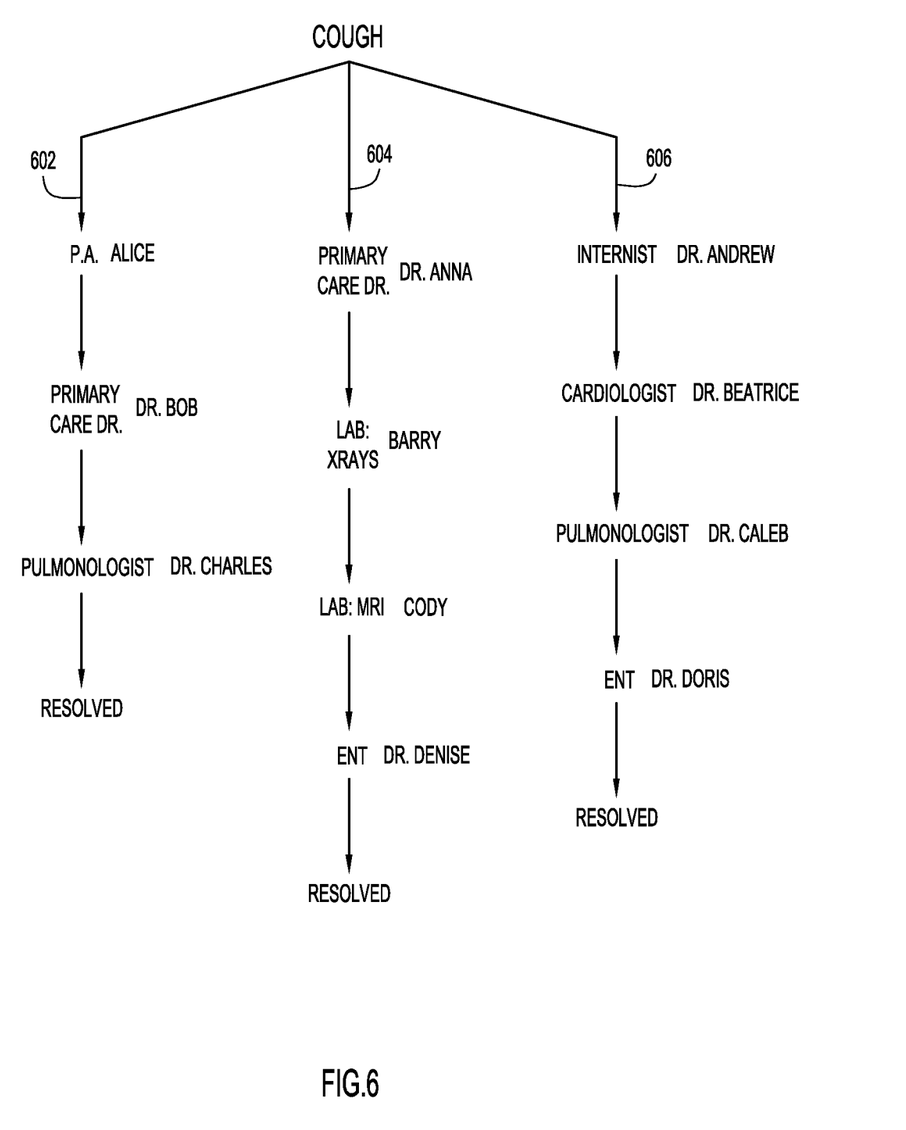
FIG. 6 shows example paths of healthcare providers associated with a resolved condition of a patient.

FIG. 6 illustrates three exemplary chains of providers that may be included in a determined network of healthcare providers. Each of the chain of providers, in this example, is associated with a medical condition, cough. Path 602 shows that a patient, "patient A", visited physician assistant, Alice, complaining of a cough. Alice referred patient A to primary care doctor, Dr. Bob. After examining patient A, Dr. Bob referred patient A to pulmonologist, Dr. Charles, who treated patient A and resolved the cough. Path 604 shows that a patient, "patient B", visited primary care doctor, Dr. Anna, complaining of a cough. Dr. Anna examined patient B and sent patient B to a lab to have chest x-rays by x-ray technician Barry and an MRI by MRI technician Cody. After the chest x-rays and the MRIs were read, patient B was referred to ENT, Dr. Denise, who resolved the cough. Path 606 shows that a patient, "patient C", visited internist, Dr. Andrew, complaining of a cough. After examining patient C, Dr. Andrew referred patient C to pulmonologist, Dr. Caleb. Dr. Caleb examined patient C and referred patient C to ENT, Dr. Doris, who resolved patient C's cough.

In an embodiment of the invention in which an electronic health record waiting for attention is selected, indicating that a patient has a cough, the embodiment may identify a shortest path from among multiple paths of providers, within the healthcare provider network, in which a patient's cough was resolved. Using paths 602, 604 and 606 as the multiple paths of providers, the embodiment may select path 602 and may present a result indicating that the patient should see physician assistant, Alice. After the patient visits Alice, an update to the patient's healthcare record may be submitted providing additional information regarding the patient's condition. For example, the medical condition, cough, may be changed to a different medical condition. As a result, another shortest path, associated with the different medical condition, may be selected and another healthcare provider may be presented for the patient to visit. If a particular healthcare provider is not available, various embodiments may find another provider who is available and who fulfills a same role.

Figure 7:
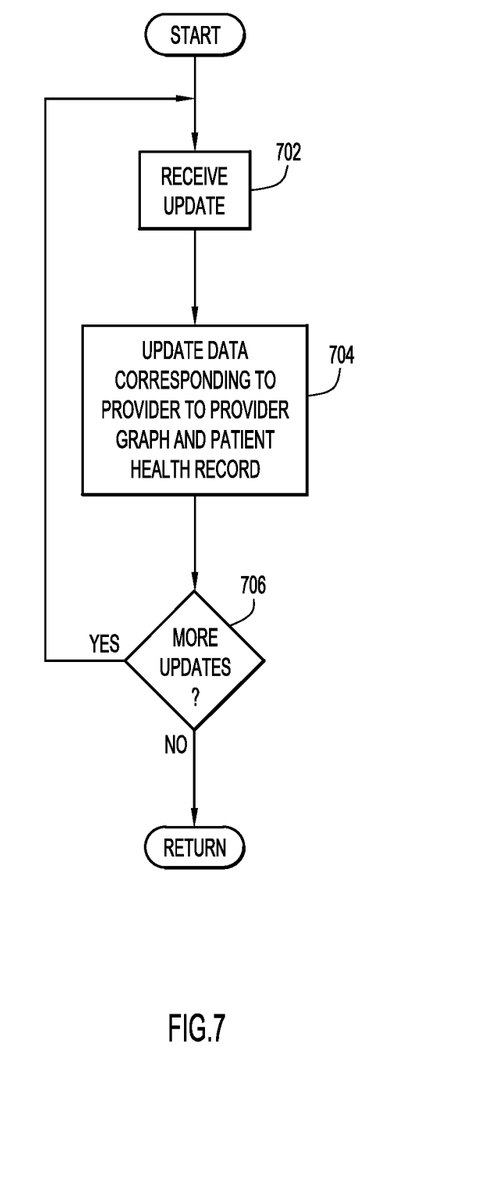
FIG. 7 is a flowchart illustrating an example process for receiving and processing updates regarding electronic health records of patients.

FIG. 7 is a flowchart of an example process that may be performed in various embodiments to process updates to patients' electronic health records, such as an update indicating a result of a visit to a recommended healthcare provider. The process may begin with receiving an update (act 702). After receiving the update, data corresponding to the healthcare provider graph, as well as a specific patient's electronic health record may be updated (act 704). A determination may then be made regarding whether there are additional updates to process (act 706). If no additional updates exist, then the process may be completed. Otherwise, acts 702-706 may be repeated.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim as our invention:

1. A method in a data processing system comprising at least one processor and at least one memory, the at least one memory comprising instructions executed by the at least one processor to cause the at least one processor to process electronic health records, the method comprising:
    analyzing electronic health records of patients and generating a graph of linked healthcare providers including paths each indicating a series of corresponding linked healthcare providers encountering a same patient for a same medical condition in order of occurrence;
    forming a query based on at least one medical condition from a selected electronic health record of a patient;
    generating, based on the query, a plurality of paths from the graph each indicating a series of corresponding healthcare providers visited by a respective patient that led to a successful outcome for the at least one medical condition;
    identifying a shortest path of the plurality of paths;
    determining a healthcare provider to visit for the patient associated with the selected electronic health record from the series of corresponding healthcare providers within the identified shortest path; and
    notifying the patient of the determined healthcare provider.

2. The method of claim 1, wherein the determining the healthcare provider further comprises:
    determining that the healthcare provider in the identified shortest path is unavailable; and
    in response to the determining that the healthcare provider in the identified shortest path is unavailable, substituting for the healthcare provider, from one of the plurality of paths, a different healthcare provider who has a same role as the healthcare provider and is available.

3. The method of claim 2, wherein the substituting is performed only when a record of successful outcomes of the different healthcare provider is no more than a predefined percentage less than a record of successful outcomes of the healthcare provider.

4. The method of claim 1, further comprising:
updating a medical condition in an electronic health record as a result of the patient associated with the electronic health record visiting a corresponding available healthcare provider.

5. The method of claim 4, further comprising:
determining that the updated medical condition is a different medical condition than a medical condition before the updating; and
in response to the determining that the updated medical condition is a different medical condition, performing:
forming a second query based on the updated medical condition,
generating, based on the second query, a second plurality of paths from the graph each indicating a second series of corresponding healthcare providers visited by a second respective patient that led to a successful outcome for the updated medical condition,
identifying a new shortest path of the second plurality of paths,
determining a new available healthcare provider to visit for the patient associated with the updated medical condition, and
notifying the patient of the new available healthcare provider.

6. The method of claim 1, further comprising:
automatically communicating with a scheduling system of the healthcare provider to schedule an appointment for the patient; and wherein:
the notifying notifies the patient of the scheduled appointment with the healthcare provider.

7. The method of claim 6, further comprising:
notifying a referring healthcare provider of the scheduled appointment.

8. A system for processing electronic health records comprising:
at least one processor; and
at least one memory connected to the at least one processor, the at least one memory including instructions for the at least one processor to configure the system to:
analyze electronic health records of patients and generate a graph of linked healthcare providers including paths each indicating a series of corresponding linked healthcare providers encountering a same patient for a same medical condition in order of occurrence;
form a query based on at least one medical condition from a selected electronic health record of a patient;
generate, based on the query, a plurality of paths from the graph each indicating a series of corresponding healthcare providers visited by a respective patient that led to a successful outcome for the at least one medical condition;
identify a shortest path of the plurality of paths;
determine a healthcare provider to visit for the patient associated with the selected electronic health record from the series of corresponding healthcare providers within the identified shortest path; and
notify the patient of the determined healthcare provider.

9. The system of claim 8, wherein the at least one memory further includes instructions for the at least one processor to configure the system to:
determine that the healthcare provider in the identified shortest path is unavailable; and
in response to the determining that the healthcare provider in the identified shortest path is unavailable, substituting for the healthcare provider, from one of the plurality of paths, a different healthcare provider who has a same role as the healthcare provider and is available.

10. The system of claim 9, wherein the substituting is performed only when a record of successful outcomes of the different healthcare provider is no more than a predefined percentage less than a record of successful outcomes of the healthcare provider.

11. The system of claim 8, wherein the at least one memory further includes instructions for the at least one processor to configure the system to:
update a medical condition in an electronic health record as a result of the patient associated with the electronic health record visiting a corresponding available healthcare provider.

12. The system of claim 11, wherein the at least one memory further includes instructions for the at least one processor to configure the system to:
determine that the updated medical condition is a different medical condition than a medical condition before the updating; and
in response to the determining that the updated medical condition is a different medical condition:
form a second query based on the updated medical condition,
generate, based on the second query, a second plurality of paths from the graph each indicating a second series of corresponding healthcare providers visited by a second respective patient that led to a successful outcome for the updated medical condition,
identify a new shortest path of the second plurality of paths,
determine a new available healthcare provider to visit for the patient associated with the updated medical condition, and
notify the patient of the new available healthcare provider.

13. The system of claim 8, wherein the at least one memory further includes instructions for the at least one processor to configure the system to:
automatically communicate with a scheduling system of the healthcare provider to schedule an appointment for the patient; and wherein:
the notifying notifies the patient of the scheduled appointment with the healthcare provider.

14. The system of claim 13, wherein the at least one memory further includes instructions for the at least one processor to configure the system to:
notify a referring healthcare provider of the scheduled appointment.

15. A computer program product comprising:
at least one non-transitory computer readable storage medium having computer readable program code embodied therewith for execution on a processing system, the computer readable program code being configured to be executed by the processing system to:
analyze electronic health records of patients and generate a graph of linked healthcare providers including paths each indicating a series of corresponding linked healthcare providers encountering a same patient for a same medical condition in order of occurrence;

form a query based on at least one medical condition from a selected electronic health record of a patient;

generate, based on the query, a plurality of paths from the graph each indicating a series of corresponding healthcare providers visited by a respective patient that led to a successful outcome for the at least one medical condition;

identify a shortest path of the plurality of paths;

determine a healthcare provider to visit for the patient associated with the selected electronic health record from the series of corresponding healthcare providers within the identified shortest path; and notify the patient of the determined healthcare provider.

16. The computer program product of claim 15, wherein the computer readable program code is further configured to be executed by the processing system to:

determine that the healthcare provider in the identified shortest path is unavailable; and in response to the determining that the healthcare provider in the identified shortest path is unavailable, substituting for the healthcare provider, from one of the plurality of paths, a different healthcare provider who has a same role as the healthcare provider and is available.

17. The computer program product of claim 16, wherein the substituting is performed when a record of successful outcomes of the different healthcare provider is no more than a predefined percentage less than a record of successful outcomes of the healthcare provider.

18. The computer program product of claim 15, wherein the computer readable program code is further configured to be executed by the processing system to:

update a medical condition in an electronic health record as a result of the patient associated with the electronic health record visiting a corresponding available healthcare provider.

19. The computer program product of claim 18, wherein the computer readable program code is further configured to be executed by the processing system to:

determine that the updated medical condition is a different medical condition than a medical condition before the updating;

in response to the determining that the updated medical condition is a different medical condition:

form a second query based on the updated medical condition, generate, based on the second query, a second plurality of paths from the graph each indicating a second series of corresponding healthcare providers visited by a second respective patient that led to a successful outcome for the updated medical condition, identify a new shortest path of the second plurality of paths, determine a new available healthcare provider to visit for the patient associated with the updated medical condition, and notify the patient of the new available healthcare provider.

20. The computer program product of claim 15, wherein the computer readable program code is further configured to be executed by the processing system to:

automatically communicate with a scheduling system of the healthcare provider to schedule an appointment for the patient; and wherein:

the notifying notifies the patient of the scheduled appointment with the healthcare provider.

* * * * *